United States Patent [19]

Andrillon et al.

[11] 4,065,255
[45] Dec. 27, 1977

[54] 2-METHYL-5-N-HYDROXYALKYLAMINO-PHENOL IN AN OXIDATION DYE COMPOSITION AND METHOD OF USING THE SAME

[75] Inventors: Patrick Andrillon, Aulnay-sous-Bois; Andree Bugaut, Boulogne-Billancourt, both of France

[73] Assignee: L'Oreal, Paris, France

[21] Appl. No.: 699,169

[22] Filed: June 23, 1976

[30] Foreign Application Priority Data

June 26, 1975  France ............................. 75.20154

[51] Int. Cl.$^2$ ............................................. A61K 7/13
[52] U.S. Cl. ............................................. 8/10.2; 8/11; 8/32; 260/573
[58] Field of Search .......................... 8/10.2, 11, 32

[56] References Cited

U.S. PATENT DOCUMENTS

| B 430,334 | 1/1976 | Halasz et al. ........................ 8/10.2 |
| 3,210,252 | 10/1965 | Blanke et al. ........................ 8/10.2 |
| 3,337,411 | 8/1967 | Wilmsmann et al. ................. 8/10.2 |
| 3,415,608 | 12/1968 | Tucker ................................... 8/10.2 |
| 3,712,790 | 1/1973 | Kalopissis et al. .................... 8/10.2 |
| 3,730,677 | 5/1973 | Kalopissis et al. .................... 8/10.2 |
| 3,834,866 | 9/1974 | Pum ................................. 8/10.2 X |
| 3,893,803 | 7/1975 | Kaiser ................................... 8/10.2 |

Primary Examiner—Albert T. Meyers
Assistant Examiner—Vera C. Clarke
Attorney, Agent, or Firm—Cushman, Darby & Cushman

[57]  ABSTRACT

A dye composition for keratinic fibers comprises in an aqueous or hydroalcoholic solution at least one coupler of the formula

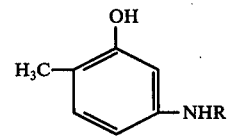

wherein R is hydroxyalkyl containing 1-4 carbon atoms, and at least one oxidation base.

21 Claims, No Drawings

2-METHYL-5-N-HYDROXYALKYLAMINO-PHENOL IN AN OXIDATION DYE COMPOSITION AND METHOD OF USING THE SAME

The present invention relates to a composition for dyeing keratinic fibers, and particularly living human hair, the said composition being employed in a process for achieving an oxidation or permanent coloration of the hair.

This type of hair coloration has been known for a number of years, and it is generally characterized by the fact that it has the ability to impart to white hair an extremely wide variety of shades or colors which are highly stable over a relatively long period of time. It is this feature, i.e. its stability or durability over a prolonged period of time which differentiates this type of coloration from a semi-permanent or temporary type coloration which is most often employed simply to add a variety of glints to the natural color of the hair or to lightly cover the hair in its natural tones.

Oxidation dye compositions are generally mixtures of an "oxidation base" compound such as para and/or ortho phenylene diamines or para and/or ortho amino phenols substituted or not, and a "coupler" compound or a coupling agent which can be a meta diamine, a metaamino phenol or a meta diphenol.

In a general fashion, it is known that different shades can be obtained depending upon the particular oxidation base and coupler employed. It is also known, however, that difficulties are encountered in the use of certain bases or certain couplers since the resulting colorations achieved often are not stable with time and often either the base or the coupler component decomposes during storage, which can cause a modification in the otherwise expected color.

It has also been observed in known oxidation dye systems that colors formed in situ during the application of the dye composition to the hair can undergo some alteration or modification on exposure to light or after one or more shampooings.

Such a system, employing as a coupler 2-methyl-5-amino phenol, has been known to produce one or more of these disadvantages.

In an attempt to overcome these disadvantages, efforts have been directed to the production of substituted metaamino phenols and more particularly those carrying a substituted amino group so as to cause either a displacement of the absorption spectrum of the final color, or to assist the speed of coupling of said couplers with the greatest possible number of oxidation bases so as to obtain more clear and more reproducible colors.

However, most of these efforts have been relatively ineffectual since certain compounds either give colors only slightly stable with time or lack acceptable storage stability characteristics, especially when present in an ammoniacal dye medium which is conventionally employed in an oxidation type dyeing operation.

Further, it has been observed that the attainment of stable indophenols, indamines or indoanilines does not necessarily mean that intermediate compounds will exhibit comparable or even acceptable stability characteristics during storage or that the color obtained using the same is completely predictable.

The present invention relates to a hair dye composition which overcomes the above disadvantages, the said composition containing a coupler compound having the formula

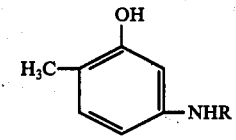

wherein R represents hydroxyalkyl containing between 1 to 4 carbon atoms and more particularly β-hydroxyethyl, and in combination therewith a conventional oxidation base. The oxidation dye composition of the present invention is stable under conventional storage conditions and provides on the addition thereto of an oxidizing agent, colors which are highly resistant to washing, to weather and to light.

Thus one object of the present invention is the provision of a dye composition for keratinic fibers, and in particular for living human hair which contains at least one coupler having the formula

wherein R represents hydroxyalkyl containing 1–4 carbon atoms and preferably β-hydroxyethyl, and an oxidation base selected from the group consisting of a compound having the formula

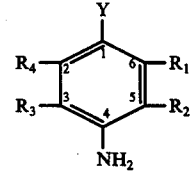

wherein $R_1$, $R_2$, $R_3$ and $R_4$ each independently represent hydrogen, alkyl containing 1–4 carbon atoms, halogen and alkoxy containing 1–4 carbon atoms, Y represents OH or

wherein $R_5$ and $R_6$ each independently represent a member selected from the group consisting of hydrogen, alkyl, hydroxyalkyl, carbamylalkyl, mesylaminoalkyl, aminoalkyl, acylaminoalkyl, sulfoalkyl, morpholinoalkyl, piperidinoalkyl, monoalkylaminoalkyl, dialkylaminoalkyl, arylsulfonamido alkyl and carboxyalkyl, wherein each of said alkyl moieties contains from 1–4 carbon atoms and wherein said acyl moiety is preferably acetyl and wherein said aryl moiety is preferably phenyl or naphthyl and a heterocyclic compound carrying in para position on the heterocyclic ring thereof either two amino groups, or an amino group and a hydroxy group. The oxidation bases employed in the present invention can be provided in the form of a free base or in the form of an acid addition salt such as a hydrochloride, a hydrobromide or a sulfate.

Another object of the present invention is a process for dyeing hair using the above-mentioned compositions.

The compositions in accordance with the present invention produce original shades or colors which exhibit good stability to washing, to light and to weather.

The colors are accurately reproducible because of the very great stability characteristics of the above-defined coupler, particularly in an ammoniacal dye composition solution.

Generally the use of paraphenylene diamines in the present invention as the oxidation base produces colors ranging from violet red to blue violet; the use of paraamino phenols as the oxidation base produces coppery oranges.

Further, in the same hair dye composition, the coupler of formula (I) and both a paraamino phenol and a paraphenylene diamine of formula (II) can be combined so as to obtain, depending on the choice of the paraphenylene diamine or the paraamino phenol, a whole range of shades.

Moreover, there can also be combined with the coupler of formula (I) other conventional couplers such as metadiphenols, metaamino phenols or their derivatives or even heterocyclic couplers of the morpholine, pyridine or pyrazoline series or even diketone type couplers.

Representative oxidation bases of formula (II) useful in the compositions of the present invention include for instance:

2-methyl-4-amino-N-$\beta$-mesylaminoethyl aniline sulfate;
3-methoxy-4-amino-N,N-dimethyl aniline sulfate;
2,6-dimethyl-4-amino phenol;
4-amino-N-acetylamino ethyl aniline sulfate;
3-methyl-4-amino-N,N-ethyl, carbamylmethyl aniline;
3-methyl-4-amino-N,N-ethyl, $\beta$-mesylaminoethyl aniline;
N-methyl paraphenylene diamine dihydrochloride;
paratoluylene diamine dihydrochloride;
paraamino phenol;
2,6-dimethyl-3-methoxy paraphenylene diamine dihydrochloride;
2-methyl-5-methoxy paraphenylene diamine dihydrochloride;
2-methoxy-4-amino-N,$\beta$-hydroxyethyl aniline sulfate;
4-amino-N-$\beta$-mesylaminoethyl aniline sulfate;
2,5-dimethyl-4-amino phenol;
paraphenylene diamine;
methoxy paraphenylene diamine dihydrochloride;
4-amino-N,N-ethyl, carbamylmethyl aniline;
4-amino-N,N-di-$\beta$-hydroxyethyl aniline sulfate;
N,N-dimethyl paraphenylene diamine dihydrochloride;
chloroparaphenylene diamine;
3-methyl-4-amino-N-methyl aniline dihydrochloride;
3-methoxy-4-amino-N-methyl aniline dihydrochloride;
4-amino-N,$\beta$-hydroxyethyl aniline sulfate;
2-chloro-4-amino-N-methyl aniline sulfate;
2-methyl-4-amino-N-methyl aniline sulfate;
2-methoxy-4-amino-N-carbamyl methyl aniline;
4-amino-N,N-ethyl, $\beta$-piperidinoethylaniline trihydrochloride;
4-amino-N,N-ethyl, $\beta$-sulfoethyl aniline;
3-methoxy-4-amino-N-$\beta$-hydroxyethyl aniline sulfate;
2-chloro-4-amino-N-acetylaminoethyl aniline sulfate;
2-methyl-4-amino-N-$\beta$-hydroxyethyl aniline sulfate;
3-methyl-4-amino-N,N-ethyl, $\beta$-sulfoethyl aniline;
3-methyl-4-amino phenol hydrobromide;
2,5-diamino pyridine dihydrochloride; and
2,4-dihydroxy-5,6-diamino pyrimidine.

The hair dye composition of the present invention generally contains the coupler of formula (I) in an amount ranging preferably between 0.01 and 2.5 percent by weight thereof. The oxidation base, and more particularly the oxidation base of formula (II) is present in an amount ranging between 0.01 and 3.5 percent by weight thereof. The molar ratio of coupler:oxidation base ranges between 5:1 and 1:5.

These hair dye compositions can also include other dyes such as anthraquinone dyes, nitrobenzene dyes, diphenylamine dyes, azo dyes, indoanilines, indophenols and indamines.

The dye compositions of the present invention employ as a carrier or vehicle therefor an aqueous or hydroalcoholic solution where in the latter the alcoholic component can be a lower alkanol, preferably ethanol or isopropanol, or a glycol such as butyl glycol, the monoethyl ester of diethylene glycol, and the like. The alcoholic portion of the hydroalcoholic solution is generally present in an amount up to 40 weight percent and preferably from about 1-40 weight percent of said solution.

The hair dye composition can also contain a cationic, an anionic or an amphoteric surface active agent in an amount ranging up to 20 weight percent preferably about 1-20 weight percent. Representative surface active agents include fatty alcohol sulfates, fatty acid ethanolamides, or a polyoxyethylenated acid or alcohol. A thickening agent, such as carboxymethyl cellulose can also be present as can higher fatty alcohols.

Moreover the hair dye compositions of the present invention can contain an oxidizing agent such as $H_2O_2$, urea peroxide or persalt such as ammonium persulfate.

Finally, the hair dye composition can also include one or more of a perfume, an antioxidant agent, a sequestering agent, an alkalinizing agent such as ammonia, sodium phosphate, sodium carbonate or a lower alkanolamine such as methanolamine and ethanolamine, and an acidifying agent such as phosphoric acid, lactic acid, acetic acid, and the like. The antioxidant can advantageously be sodium bisulfite. The pH of the hair dye composition of the present invention ranges between 7 and 11.

The present invention also relates to a process for dyeing keratinic fibers, particularly living human hair, using the above-defined composition.

In accordance with a first embodiment of the invention, a cosmetic hair dye composition containing both the coupler of formula (I) and an oxidation base, preferably one of formula (II) is initially prepared. At the moment of use, an oxidizing agent such as $H_2O_2$, urea peroxide or a persalt, and in particular a cosmetic oxidizing agent such as $H_2O_2$ is admixed with the coupler-oxidation base system and the resulting admixture is thoroughly homogenized. The resulting homogeneous composition is then applied to the keratinic fibers and is permitted to remain in contact therewith for a of time ranging between 3 and 30 minutes. The hair is then rinsed, shampooed and dried.

In accordance with another embodiment of the present invention, there is initially applied to the hair, either a solution containing the coupler and then a solution containing the oxidation base, or a solution containing the oxidation base and then a solution containing the coupler. The oxidizing agent in either case is added at the moment of use with the secondly applied solution. The period of contact of the hair with each solution is about 3 to 30 minutes.

Moreover, it is possible to apply, successively, either the solution containing the oxidation base then the solution containing the coupler, or the solution containing the coupler then the solution containing the oxidation base. In either instance, this dual application procedure is followed by the application of an oxidizing agent, such as $H_2O_2$.

Preparation of 2-methyl-5-N-$\beta$-hydroxyethylamino phenol in accordance with the following reaction scheme:

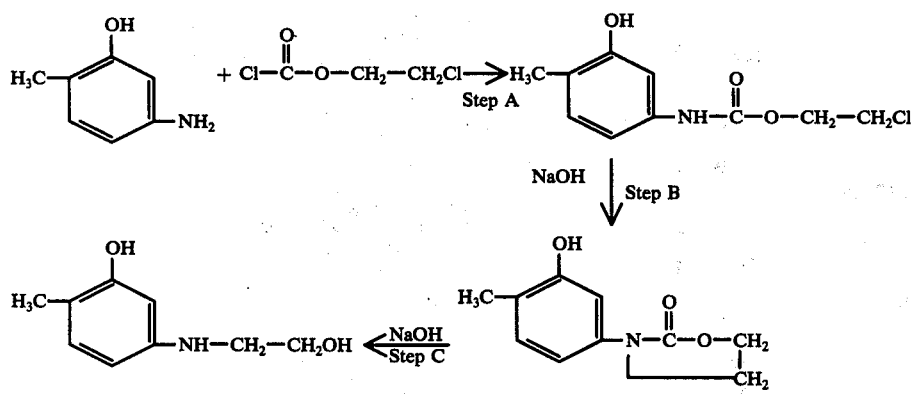

A. Preparation of [(4'-methyl-5'-hydroxy)phenyl] $\beta$-chloroethyl carbamate.

0.5 mole (61.5 g) of 2-methyl-5-amino phenol is dissolved in 246 cc of dioxan. 0.275 mole (27.5 g) of calcium carbonate is then added and the temperature of the resulting mixture is raised to about 90° C. There is then introduced, with agitation, 0.55 mole (78.7 g) of $\beta$-chloroethyl chloroformate. At the end of this addition, the reaction medium is maintained, with agitation, for one hour at 90° C. After cooling the reaction mixture, the same is filtered to remove mineral salts after which one liter of ice water is added thereto. [(4'-methyl-5'-hydroxy)phenyl]$\beta$-chloroethyl carbamate is then filtered, washed with water, recrystallized in a mixture of benzene and cyclohexane and dried under a vacuum, the product melts at 100° C.

| Elemental analysis: $C_{10}H_{12}NO_3Cl$ | | |
|---|---|---|
| | Calculated | Found |
| C% | 52.40 | 52.44 |
| H% | 5.24 | 5.30 |
| N% | 6.10 | 6.01 |
| Cl% | 15.48 | 15.30 – 15.33 |

B - Preparation of N-[(4'-methyl-5'-hydroxy)phenyl]-1,3-oxazolidine-2-one.

The crude $\beta$-chloroethyl carbamate obtained in accordance with the preceding operation is introduced into 233 cc of a 4.3N NaOH solution at 45° C. The resulting reaction mixture is stirred for 20 minutes at which time it is then added to 200 cc of water cooled to 0° C to which is added a sufficient amount of HCl to precipitate N-[(4'-methyl-5'-hydroxy)phenyl]-1,3-oxazolidine-2-one.

After recrystallization of the said precipitate in ethyl alcohol at 95° C and drying under a vacuum, the product melts at 180° C.

| Elemental analysis: $C_{10}H_{11}O_3N$ | | |
|---|---|---|
| | Calculated | Found |
| C% | 62.16 | 62.64 |
| H% | 5.74 | 5.92 |
| N% | 7.25 | 7.35 |

C - Preparation of 2-methyl-5-N-$\beta$-hydroxyethyl amino phenol.

0.35 mole (67.55 g) of N-[(4'-methyl-5'-hydroxy) phenyl]-1,3-oxazolidine-2-one is admixed with 200 cc of a 5N NaOH solution at 70° C, and the mixture is stirred for 30 minutes. The reaction mixture is then cooled to 0° C and neutralized by the addition of acetic acid so as to precipitate the desired product in crystal form. The product which is then filtered, washed with water, recrystallized in water and dried under a vacuum, melts at 90° C.

| Elemental analysis: $C_9H_{13}O_2N$ | | |
|---|---|---|
| | Calculated | Found |
| C% | 64.65 | 64.43 |
| H% | 7.84 | 7.50 |
| N% | 8.38 | 8.40 |

Table I

Examples of Compositions

The following hair dye compositions are prepared:

No. 1

| | | |
|---|---|---|
| Paratoluylene diamine dihydrochloride | 1.17 | g |
| 2-methyl-5-N-$\beta$-hydroxy-ethylamino phenol | 1 | g |
| Sodium lauryl sulfate with 19% of the starting alcohol being oxyethylenated | 20 | g |
| Ethylene diamine tetra-acetic acid, sold under the mark Trilon B | 0.2 | g |
| Ammonia - >° Bé | 10 | g |
| Sodium bisulfite, 40% solution | 1 | g |
| Water, q.s.p. | 100 | g |
| pH = 10.5 | | |

No. 2

| | | |
|---|---|---|
| N,N-di-$\beta$-hydroxyethyl paraphenylene diamine sulfate | 0.735 | g |
| 2-methyl-5-N-$\beta$-hydroxy-ethylamino phenol | 0.5 | g |
| Ammonium lauryl sulfate | 10 | g |
| Ammonia - 22° Bé | 12 | g |
| Water, q.s.p | 100 | g |

Table I-continued
Examples of Compositions
The following hair dye compositions are prepared:

No. 3

| Component | Amount | Unit |
|---|---|---|
| 4-amino-N,N-ethyl, carbamylmethyl aniline | 1.35 | g |
| 2-methyl-5-N-β-hydroxy-ethylamino phenol | 1.17 | g |
| Lauryl alcohol oxyethylenated with 10.5 moles of ethylene oxide | 5 | g |
| Butyl glycol | 5 | g |
| Ammonia - 22° Bé | 10 | g |
| Water, q.s.p. | 100 | g |
| pH = 10 | | |

No. 4

| Component | Amount | Unit |
|---|---|---|
| Paraphenylene diamine dihydrochloride | 0.905 | g |
| 2-methyl-5-N-β-hydroxy-ethylamino phenol | 0.835 | g |
| Ammonium alkyl sulfate, wherein the alkyl moiety contains $C_{12}$ and $C_{14}$, non-oxyethylenated (70% $C_{12}$, 30% $C_{14}$) | 15 | g |
| Lauryl alcohol oxyethylenated with 10.5 moles of ethylene oxide | 5 | g |
| Ammonia - 22° Bé | 10 | g |
| Water, q.s.p. | 100 | g |
| pH = 10 | | |

No. 5

| Component | Amount | Unit |
|---|---|---|
| 4-amino-3-methyl-N,N-ethyl, β-sulfoethyl aniline | 2.58 | g |
| 2-methyl-5-N-β-hydroxy-ethylamino phenol | 1.67 | g |
| Lauryl alcohol oxyethylenated with 10.5 moles of ethylene oxide | 5 | g |
| Triethanolamine, q.s.p. pH = 7 | | |
| Water, q.s.p. | 100 | g |

No. 6

| Component | Amount | Unit |
|---|---|---|
| 3-methyl-4-amino-N-ethyl aniline dihydrochloride | 0.0125 | g |
| 2-methyl-5-N-β-hydroxy-ethylamino phenol | 0.01 | g |
| Ethanol (96° titer) | 20 | g |
| Ammonia - 22° Bé | 5 | g |
| Water, q.s.p. | 100 | g |
| pH = 10 | | |

No. 7

| Component | Amount | Unit |
|---|---|---|
| Chloroparaphenylene diamine | 0.214 | g |
| 2-methyl-5-N-β-hydroxy-ethylamino phenol | 0.25 | g |
| Ethylenediamine tetraacetic acid, sold under the mark Trilon B | 0.2 | g |
| Sodium bisulfite - 40% solution | 1 | g |
| Sodium lauryl sulfate with 19% of the starting alcohol being oxyethylenated | 20 | g |
| Ammonia - 22 Bé | 10 | g |
| Water, q.s.p. | 100 | g |
| pH = 10.5 | | |

No. 8

| Component | Amount | Unit |
|---|---|---|
| N-ethyl paraphenylene diamine dihydrochloride | 0.836 | g |
| 2-methyl-5-N-β-hydroxy-ethylamino phenol | 0.67 | g |
| Lauryl alcohol oxyethylenated with 10.5 moles of ethylene oxide | 5 | g |
| Ammonia - 22° Bé | 15 | g |
| Water, q.s.p. | 100 | g |

No. 9

| Component | Amount | Unit |
|---|---|---|
| 2-methyl-4-amino-N-carbamyl-methyl aniline hydrobromide | 1.3 | g |
| 2-methyl-5-N-β-hydroxy-ethylamino phenol | 0.835 | g |
| Butyl glycol | 20 | g |
| Acrylic acid polymer, MW - 2 to 3 million, sold under the mark "Carbopol 934" | 3.6 | g |
| Ammonia - 22° Bé q.s.p. pH = 9.5 | | |
| Water, q.s.p. | 100 | g |

No. 10

| Component | Amount | Unit |
|---|---|---|
| 2-methyl-5-N-β-hydroxy-ethylamino phenol | 2.5 | g |
| 2,5-dimethyl-3-methoxy paraphenylene diamine dihydrochloride | 3.58 | g |
| Butyl glycol | 20 | g |
| Diethanolamide of the fatty acids of copra | 8 | g |
| Ammonia - 22° Bé | 14 | g |
| Water, q.s.p. | 100 | g |

No. 11

| Component | Amount | Unit |
|---|---|---|
| Paraamino phenol | 0.545 | g |
| 2-methyl-5-N-β-hydroxy-ethylamino phenol | 0.835 | g |
| Sodium lauryl sulfate with 19% of the starting alcohol being oxyethylenated | 20 | g |
| Ethylene diamine tetraacetic acid, sold under the mark Trilon B | 0.2 | g |
| Ammonia - 22° Bé q.s.p. pH = 10 | | |
| Water, q.s.p. | 100 | g |

No. 12

| Component | Amount | Unit |
|---|---|---|
| 2,5-dimethyl paraphenylene diamine dihydrochloride | 0.5 | g |
| Methoxy paraphenylene diamine dihydrochloride | 0.2 | g |
| 3-chloro-4-amino phenol hydrochloride | 0.3 | g |
| 6-hydroxy phenomorpholine | 0.53 | g |
| 2-methyl-5-N-β-hydroxy-ethylamino phenol | 0.12 | g |
| Butyl glycol | 5 | g |
| Lauryl alcohol oxyethylenated with 10.5 moles of ethylene oxide | 5 | g |
| Ammonia - 22° Bé | 10 | g |
| Water, q.s.p. | 100 | g |
| pH = 10 | | |

No. 13

| Component | Amount | Unit |
|---|---|---|
| Paratoluylene diamine dihydrochloride | 1.5 | g |
| 3-methyl-4-amino-N,N-(ethyl, carbamylmethyl) paraphenylene diamine | 0.3 | g |
| Paraamino phenol | 0.7 | g |
| 2,4-diamino anisole dihydrochloride | 0.3 | g |
| Resorcinol | 0.42 | g |
| 2-methyl-5-N-β-hydroxy-ethylamino phenol | 0.40 | g |
| Sodium lauryl sulfate with 19% of the starting alcohol being oxyethylenated | 20 | g |
| Ethylene diamine tetraacetic acid, sold under the mark Trilon B | 0.2 | g |
| Ammonia - 22° Bé | 10 | g |
| Sodium bisulfite - 40% solution | 1 | g |
| Water, q.s.p. | 100 | g |
| pH = 10.5 | | |

No. 14

| Component | Amount | Unit |
|---|---|---|
| 4-amino-N-β-hydroxy-ethyl aniline sulfate | 0.20 | g |
| 2-methyl-5-N-β-hydroxy-ethylamino phenol | 0.67 | g |
| Ethanol (96° titer) | 40 | g |
| Triethanolamine, q.s.p. pH = 7 | | |
| Water, q.s.p. | 100 | g |

No. 15

| Component | Amount | Unit |
|---|---|---|
| 2-methyl-5-methoxy paraphenylene diamine dihydrochloride | 1.2 | g |
| 6-hydroxy phenomorpholine | 0.42 | g |
| 1-γ-aminopropylamino anthraquinone | 0.30 | g |
| Nitrometaphenylene diamine | 0.1 | g |
| 4'-N,N-dimethylamino-4-hydroxy diphenylamine hydrochloride | 0.3 | g |
| Diglycerolated oleyl alcohol | 2.8 | g |
| 2-methyl-5-N-β-hydroxy-ethylamino phenol | 0.5 | g |
| Tetraglycerolated oleyl alcohol | 4.2 | g |
| Propylene glycol | 30 | g |
| Ammonia - 22° Bé, q.s.p. pH = 10 | | |
| Water, q.s.p. | 100 | g |

No. 16

| Component | Amount | Unit |
|---|---|---|
| 2-methyl-5-N-β-hydroxy-ethylamino phenol | 0.83 | g |
| 4-amino-N-ethyl, β-sulfoethyl aniline | 1.22 | g |
| Butyl glycol | 5 | g |
| Lauryl alcohol oxyethylenated with 10.5 moles of ethylene oxide | 5 | g |
| Ammonia - 22° Bé, q.s.p. pH = 10 | | |
| Water, q.s.p. | 100 | g |

Table I-continued

Examples of Compositions
The following hair dye compositions are prepared:

No. 17
| | |
|---|---|
| Methoxy paraphenylene diamine dihydrochloride | 2.11 g |
| 2-methyl-5-N-β-hydroxy-ethylamino phenol | 0.334 g |
| Diglycerolated oleyl alcohol | 3 g |
| Tetraglycerolated oleyl alcohol | 4.5 g |
| Propylene glycol | 25 g |
| Ammonia - 22° Bé, q.s.p. pH - 9.5 | |
| Water, q.s.p. | 100 g |

No. 18
| | |
|---|---|
| 2-methyl-5-methoxy paraphenylene diamine dihydrochloride | 0.675 g |
| Paraamino phenol | 0.327 g |
| 2-methyl-5-N-β-hydroxy-ethylamino phenol | 0.501 g |
| Butyl glycol | 5 g |
| Lauryl alcohol oxyethylenated with 10.5 moles of ethylene oxide | 5 g |
| Ammonia - 22° Bé | 15 g |
| Water, q.s.p | 100 g |
| pH = 10.5 | |

No. 19
| | |
|---|---|
| 3-methyl-4-amino-N-methyl-aminoethyl aniline | 0.813 g |
| 2-methyl-5-N-β-hydroxy-ethylamino phenol | 2.5 g |
| Butyl glycol | 20 g |
| Nonyl phenol oxyethylenated with 4 moles of ethylene oxide | 8 g |
| Nonyl phenol oxyethylenated with 9 moles of ethylene oxide | 8 g |
| Methanolamine, q.s.p. pH = 8 | |
| Water, q.s.p. | 100 g |

No. 20
| | |
|---|---|
| 2-methyl-4-amino-N-mesyl-aminoethyl paraphenylene diamine | 1.70 g |
| 2-methyl-5-N-β-hydroxy-ethylamino phenol | 0.955 g |
| Butyl glycol | 5 g |
| Lauryl alcohol oxyethylenated with 10.5 moles of ethylene oxide | 5 g |
| Ammonia - 22° Bé q.s.p. pH = 10 | |
| Water, q.s.p. | 100 g |

The compositions as defined in Examples 1-20 above are mixed at the moment of use with an oxidizing agent conventionally employed in this field such as $H_2O_2$ or an aqueous solution of urea peroxide in the amounts and concentrations indicated in Table II below. This mixture is applied to the hair and is permitted to remain in contact therewith for a period of time ranging between 5 and 30 minutes, at a temperature ranging from ambient temperature to 35° C.

The color imparted to the hair is ascertained after rinsing and optionally shampooing the same.

Table II below lists the various application conditions and the results obtained using the compositions of Examples 1-20 above.

Table II

Examples of dyeing hair using 100 g of the compositions of Table I

| COMPO-SITION | OXIDIZING AGENT | | | APPLICATION | | | |
|---|---|---|---|---|---|---|---|
| | Name | Concentration | Quantity | Hair Treated | Temperature | Period of Contact | COLORATION |
| 1 | $H_2O_2$ | 20 volumes | 100 g | 95% naturally white | ambient | 10 min. | very dark purple |
| 2 | aqueous solution of urea peroxide | 20% | 50 g | 95% naturally white | 30° C | 10 min. | silvery glycine |
| 3 | $H_2O_2$ | 20 volumes | 100 g | bleached | ambient | 15 min. | violet |
| 4 | $H_2O_2$ | 20 volumes | 100 g | naturally white | ambient | 20 min. | egg plant |
| 5 | $H_2O_2$ | 20 volumes | 70 g | bleached | 25° C | 10 min. | silvery mauve grey |
| 6 | $H_2O_2$ | 20 volumes | 25 g | bleached | ambient | 20 min. | pearly raw silk |
| 7 | $H_2O_2$ | 20 volumes | 80 g | bleached | ambient | 20 min. | pearly salmon pink |
| 8 | aqueous solution of ammonium persulfate | 2.28 g % | 80 g | 95% white hair | ambient | 15 min | turtle grey with violet glints |
| 9 | $H_2O_2$ | 20 volumes | 80 g | 95% naturally white hair | 25° C | 10 min. | temarisk pink |
| 10 | $H_2O_2$ | 20 volumes | 100 g | 95% naturally white hair | 35° C | 20 min. | pearly pale violet |
| 11 | $H_2O_2$ | 20 volumes | 50 g | bleached hair | 20° C | 20 min. | copper |
| 12 | $H_2O_2$ | 20 volumes | 100 g | 95% naturally white hair | ambient | 20 min. | metallic grey |
| 13 | $H_2O_2$ | 20 volumes | 100 g | 95% naturally white hair | ambient | 20 min. | deep chestnut with violet glints |
| 14 | $H_2O_2$ | 20 volumes | 30 g | 95% naturally white hair | 35° C | 20 min. | deep plum |
| 15 | $H_2O_2$ | 20 volumes | 80 g | 95% naturally white hair | ambient | 15 min. | bottle green |
| 16 | $H_2O_2$ | 20 volumes | 60 g | 95% naturally white hair | 30° C | 15 min. | ash beige with mauve glints |
| 17 | $H_2O_2$ | 20 volumes | 100 g | 95% naturally white hair | ambient | 20 min. | grey violet |
| 18 | $H_2O_2$ | 20 volumes | 100 g | 95% naturally white hair | ambient | 25 min. | deep being with mauve shade |
| 19 | $H_2O_2$ | 20 volumes | 40 g | bleached hair | ambient | 15 min. | bluish silver grey |
| 20 | aqueous solution of urea peroxide | 25 % | 30 g | bleached hair | ambient | 10 min. | pearly light parme |

What is claimed is:

1. A dye composition for keratinic fibers containing an aqueous or hydroalcoholic carrier, at least one coupler of the formula

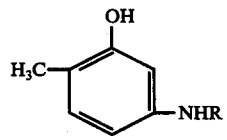

(I)

wherein R represents hydroxyalkyl having 1-4 carbon atoms and at least one oxidation base selected from the group consisting of a paraphenylene diamine, an orthophenylene diamine, a paraamino phenol, an ortho amino phenol and a heterocyclic oxidation base, said coupler being present in an amount of 0.01 to 2.5 weight percent and said oxidation base being present in an amount of 0.01 to 3.5 weight percent, based on the total weight of said composition.

2. A dye composition for human hair containing an aqueous or hydroalcoholic carrier, at least one coupler of the formula

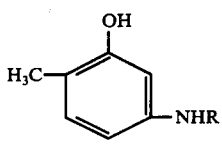

wherein R represents hydroxyalkyl having 1–4 carbon atoms and at least one oxidation base selected from the group consisting of an oxidation base having the formula

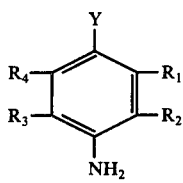

wherein $R_1$, $R_2$, $R_3$ and $R_4$ each independently are selected from the group consisting of hydrogen, alkyl having 1–4 carbon atoms, halogen and alkoxy having 1–4 carbon atoms;
Y represent OH or

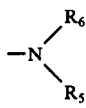

wherein $R_5$ and $R_6$ each independently represent a member selected from the group consisting of hydrogen, alkyl, hydroxyalkyl, carbamylalkyl, mesylaminoalkyl, aminoalkyl, acylaminoalkyl, sulfoalkyl, morpholinoalkyl, piperidinoalkyl, monoalkylaminoalkyl, dialkylaminoalkyl, arylsulfonamidoalkyl and carboxyalkyl wherein each of the alkyl moieties contains from 1–4 carbon atoms, and an oxidation base having a heterocyclic nucleus carrying in para position either two amino groups or an amino group and a hydroxyl group, said oxidation base being in the free base form or in the form of an acid addition salt selected from the group consisting of hydrochloride, hydrobromide and sulfate, said coupler being present in an amount of 0.01 to 2.5 weight percent and said oxidation base being present in an amount of 0.01 to 3.5 weight percent, based on the total weight of said composition.

3. The composition of claim 1 wherein said coupler has the formula

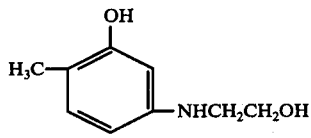

4. The composition of claim 1 wherein said oxidation base is selected from the group consisting of
2-methyl-4-amino-N-β-mesylaminoethyl aniline sulfate;
3-methoxy-4-amino-N,N-dimethyl aniline sulfate;
2,6-dimethyl-4-amino phenol;
4-amino-N-acetylaminoethyl aniline sulfate;
3-methyl-4-amino-N,N-ethyl, carbamyl methyl aniline;
3-methyl-4-amino-N,N-ethyl, β-mesylaminoethyl aniline;
N-methylparaphenylene diamine dihydrochloride;
paratoluylene diamine dihydrochloride;
paraamino phenol;
2,6-dimethyl-3-methoxy paraphenylene diamine dihydrochloride;
2-methyl-5-methoxy paraphenylene diamine dihydrochloride;
2-methoxy-4-amino-N-β-hydroxyethyl aniline sulfate;
4-amino-N-β-mesylaminoethyl aniline sulfate;
2,5-dimethyl-4-amino phenol;
methoxy paraphenylene diamine dihydrochloride;
paraphenylene diamine;
4-amino-N,N-ethyl, carbamylmethyl aniline;
4-amino-N,N-di-β-hydroxyethyl aniline sulfate;
N,N-dimethylparaphenylene diamine dihydrochloride;
chloroparaphenylene diamine;
3-methyl-4-amino-N-methyl aniline dihydrochloride;
3-methoxy-4-amino-N-methyl aniline dihydrochloride;
4-amino-N-β-hydroxyethyl aniline sulfate;
2-chloro-4-amino-N-methyl aniline sulfate;
2-methyl-4-amino-N-methyl aniline sulfate;
2-methoxy-4-amino-N-carbamyl methyl aniline;
4-amino-N,N-ethyl, β-piperidinoethyl aniline trihydrochloride;
4-amino-N,N-ethyl, β-sulfoethylaniline;
3-methoxy-4-amino-N-β-hydroxyethyl aniline sulfate;
2-chloro-4-amino-N-acetylaminoethyl aniline sulfate;
2-methyl-4-amino-N-β-hydroxyethyl aniline sulfate;
3-methyl-4-amino-N,N-ethyl, β-sulfoethyl aniline;
3-methyl-4-amino phenol hydrobromide;
2,5-diamino pyridine dihydrochloride and
2,4-dihydroxy-5,6-diamino pyrimidine.

5. The composition of claim 1 wherein the molar ratio of coupler to oxidation base ranges between 5:1 and 1:5.

6. The composition of claim 1 which also includes a hair dye selected from the group consisting of an anthraquinone dye, a nitrobenzene dye, a diphenylamine dye, an azo dye, an indophenol, an indoaniline and an indamine.

7. The composition of claim 1 wherein the carrier is a hydroalcoholic solution containing a lower alkanol or a glycol in an amount up to 40 weight percent thereof.

8. The composition of claim 1 which also includes an alkalizing agent.

9. The composition of claim 8 wherein said alkalizing agent is ammonia, sodium phosphate, sodium carbonate or an alkanolamine.

10. The composition of claim 1 which also includes a cationic, anionic or amphoteric surface active agent present in an amount up to 20 weight percent.

11. The composition of claim 1 which also includes one or more of carboxymethyl cellulose, oxyethylenated alcohol, ethylene diamine tetraacetic acid, fatty alcohol, alkaline alkylsulfate and diethanolamide of the fatty acids of copra.

12. The composition of claim 1 which also includes at least one anti-oxidant agent.

13. The composition of claim 12 wherein said anti-oxidant agent is sodium bisulfite.

14. The composition of claim 1 which also includes one or more of a perfume, a sequesterant agent and an acidifying agent.

15. A process for dyeing human hair comprising applying an effective amount of a homogeneous mixture of a cosmetic oxidizing agent and the composition of claim 1 to the hair and permitting said mixture to remain in contact therewith for a period of 3 to 30 minutes, rinsing the hair, shampooing the hair and drying the hair.

16. A process for dyeing human hair comprising initially applying to the hair an effective amount of a solution of a coupler having the formula

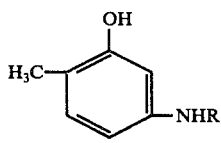

wherein R is hydroxyalkyl containing 1–4 carbon atoms, said coupler being present in an amount of 0.01 to 2.5 weight percent of said solution and then applying to the thus treated hair an effective amount of a solution of an oxidation base wherein said oxidation base is present in an amount of 0.01 to 3.5 weight percent of said solution on an oxidizing agent free basis and an effective amount of an oxidizing agent.

17. A process for dyeing human hair comprising initially applying to the hair an effective amount of a solution of an oxidation base wherein said oxidation base is present in an amount of 0.01 to 3.5 weight percent of said solution and then applying to the thus treated hair an effective amount of a solution of a coupler having the formula

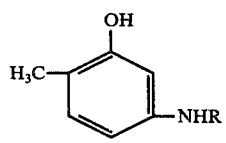

wherein R is hydroxyalkyl containing 1–4 carbon atoms, said coupler being present in an amount of 0.01 to 2.5 weight percent of said solution on an oxidizing agent-free basis and an effective amount of an oxidizing agent.

18. A process for dyeing human hair comprising initially applying to the hair an effective amount of a solution of a coupler having the formula

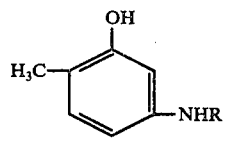

wherein R is hydroxyalkyl containing 1–4 carbon atoms, said coupler being present in an amount of 0.01 to 2.5 weight percent of said solution, then applying to the thus treated hair an effective amount of a solution of at least one oxidation base, said oxidation base being present in an amount of 0.01 to 3.5 weight percent of said solution, and finally applying to the hair an effective amount of an oxidizing agent.

19. A process for dyeing human hair comprising initially applying to the hair an effective amount of a solution of at least one oxidation base wherein said oxidation base is present in an amount of 0.01 to 3.5 weight percent of said solution, then applying to the thus treated hair an effective amount of a solution of a coupler having the formula

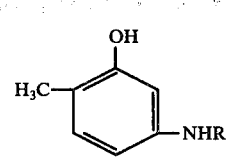

wherein R is hydroxyalkyl containing 1–4 carbon atoms, said coupler being present in an amount of 0.01 to 2.5 weight percent of said solution, and finally applying to the hair an effective amount of an oxidizing agent.

20. A dye composition for keratinic fibers containing an aqueous or hydroalcoholic carrier, at least one coupler of the formula

wherein R represents hydroxyalkyl having 1–4 carbon atoms and at least one oxidation base selected from the group consisting of a paraphenylene diamine, an orthophenylene diamine, a paraamino phenol, an ortho amino phenol and a heterocyclic oxidation base, each of said coupler and the said base being present in a hair dyeing effective amount.

21. A dye composition for human hair containing an aqueous or hydroalcoholic carrier, at least one coupler of the formula

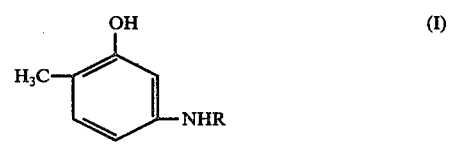

wherein R represents hydroxyalkyl having 1–4 carbon atoms and at least one oxidation base selected from the group consisting of an oxidation base having the formula

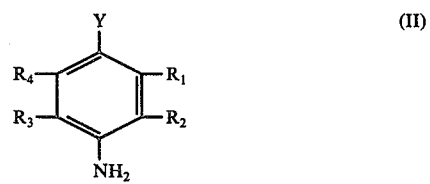

wherein $R_1$, $R_2$, $R_3$ and $R_4$ each independently are selected from the group consisting of hydrogen, alkyl having 1–4 carbon atoms, halogen and alkoxy having 1–4 carbon atoms;

Y represents OH or

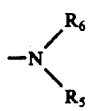

wherein $R_5$ and $R_6$ each independently represent a member selected from the group consisting of hydrogen, alkyl, hydroxyalkyl, carbamylalkyl, mesylaminoalkyl, aminoalkyl, acylaminoalkyl, sulfoalkyl, morpholinoalkyl, piperidinoalkyl, monoalkylaminoalkyl, dialkylaminoalkyl, arylsulfonamidoalkyl and carboxyalkyl wherein each of the alkyl moieties contains from 1-4 carbon atoms, and an oxidation base having a heterocyclic nucleus carrying in para position either two amino groups or an amino group and a hydroxyl group, said oxidation base being in the free base form or in the form of an acid addition salt selected from the group consisting of hydrochloride, hydrobromide and sulfate, each of the said coupler and the said base being present in a hair dyeing effective amount.

* * * * *